United States Patent [19]

Remacle

[11] Patent Number: 4,927,752
[45] Date of Patent: May 22, 1990

[54] SUPPORT USED IN BIOLUMINESCENT DOSING OF ENZYMES, SUBSTRATES OR ENZYMATIC INHIBITORS

[76] Inventor: José Remacle, Chemin des Pierres 14, B-5730 Malonne, Belgium

[21] Appl. No.: 31,470

[22] PCT Filed: Jun. 19, 1986

[86] PCT No.: PCT/BE86/00020
§ 371 Date: Feb. 20, 1987
§ 102(e) Date: Feb. 20, 1987

[87] PCT Pub. No.: WO87/00198
PCT Pub. Date: Jan. 15, 1987

[30] Foreign Application Priority Data

Jun. 26, 1985 [BE] Belgium .................................. 902745

[51] Int. Cl.$^5$ ........................ C12N 11/08; C12Q 1/66; G01N 33/53
[52] U.S. Cl. .......................................... 435/8; 435/4; 435/7; 435/15; 435/26; 435/174; 435/175; 435/180; 435/181; 435/805; 436/807; 422/52
[58] Field of Search .................. 435/4, 8, 15, 26, 174, 435/175, 180, 181, 288, 310, 7, 805, 177, 182; 436/807; 422/52; 530/354; 427/2

[56] References Cited

U.S. PATENT DOCUMENTS 4,234,681 11/1980 De Luca-McElroy ................. 435/8

FOREIGN PATENT DOCUMENTS 0134307 3/1985 European Pat. Off. ............ 435/180

Primary Examiner—Robert J. Warden
Assistant Examiner—Carol A. Spiegel
Attorney, Agent, or Firm—Fishman, Dionne & Cantor

[57] ABSTRACT

Method for the bioluminescent dosing of enzymes, substrates or enzymatic inhibitors, characterized in that there is used a transparent support made of synthetic plastic material previously treated with a charged hydrophilic substance for the Fixation by adsorption of an enzymatic system containing at least a luciferase. The invention extends to a support of the polystyrene type treated by a charged hydrophilic substance on which an enzymatic system containing at least a luciferase is fixed by adsorption.

34 Claims, No Drawings

SUPPORT USED IN BIOLUMINESCENT DOSING OF ENZYMES, SUBSTRATES OR ENZYMATIC INHIBITORS

The invention relates to an assay system consisting of a wall on which is adsorbed at least one luciferase which, by acting consecutively with one or more adsorbed or unadsorbed enzymes, enables a series of substrates, enzymes or enzyme inhibitors to be assayed by bioluminesence. This invention enables a series of biological molecules to be assayed, and is hence applicable in biochemical analyses and in medical and veterinary diagnosis.

Some luciferases are enzymes extracted from bacteria and which catalyse the reduction of flavin mononucleotide (hereinafter designated FMN) with the concomitant production of photons. These photons can be detected and measured quantitatively in photometers or by any light-sensitive detector. These luciferases can be combined with an NADH:FMN oxidoreductase or with an NADPH:FMN oxidoreductase (NADH=nicotinamide adenine dinucleotide in its reduced form; NADPH=nicotinamide adenine dinucleotide phosphate in its reduced form). Thus, it is possible, by means of these two enzymes working simultaneously, to assay NADH or NADPH in concentration regions ranging from 1 to $1000 \times 10^{-12}$ moles in the test (Stanley, P. E. Methods in Enzymology, vol. 57, pages 215–222, 1978; Lavi et al., J. Clin. Chem. Clin. Biochem., vol. 19, pages 749 and following pages, 1981).

Another luciferase is isolated from fireflies, and enables photons to be produced from the cleavage of adenosine triphosphate (ATP) to adenosine monophosphate (AMP) and pyrophosphate.

Two developments of this method have been proposed: on the one hand, the insolubilization of these two enzymes on agarose beads by coupling with cyanogen bromide, followed by the combination of these first two enzymes with a third NADH- or NADPH-dependent dehydrogenase, which enables the substrate of this latter enzyme to be measured. The main achievements are those of De Luca and his group, relating to the assay of testosterone, L-malate, D-glucose, 6-P-gluconate, L-lactate, L-alanine and L-glutamate, with a minimal assay region ranging from 1.5 to $10 \times 10^{-12}$ moles (U.S. Pat. No. 4,234,681 of M. A. De Luca-Mc Elroy; Weenhausen, G. and De Luca, M., Anal. Biochem., vol. 127, 380, 1982; Ford, J. and De Luca, M., Anal. Biochem., vol. 110, 43, 1981; Jablonski, E. and De Luca, M., Methods in Enzymology, vol. 57, 202, 1978). The 12 biliary α-hydroxy acids can also be measured (Scholemerich et al., Anal. Biochem., vol. 133, 244, 1983). The method can also be used to measure these dehydrogenases (Haggerty, C. et al., Anal. Biochem., vol. 88, 162, 1978). While this system is sensitive and specific, it nevertheless has the drawbacks of introducing a solid support (agarose or the like) into the reaction system, and this causes some retention of the emitted light and is very sensitive to agitation at the time of measuring, since the use of the porous support (agarose) requires the diffusion of the substrates into the meshes of the gel. One of the solutions proposed for these problems is to pass the solution continuously through a cell containing the gel to which these enzymes are bound (Kricka et al., Anal. Biochem., vol. 129, 392, 1983). This solution, while it deals with the disadvantages mentioned above, involves making the assay technique more complex through the use of a special apparatus.

On the other hand, recently, V. Mookambeswaren and Sunanda (European Patent 0,169,767) have proposed covalent binding of luciferase to a gel made from albumins linked to each other with glutaraldehyde.

The objective of the present invention is to remedy the disadvantages of the various systems described above, in the following manner: the invention, as characterized in the claims, consists in adsorbing the enzymes on the walls of the tube which will be introduced into the photometer, or on a strip of shape and size suitable to the measuring apparatus which can be a simple photographic film. This adsorption will be accomplished via a layer of polylysine or of a copolymer of polylysine with another charged hydrophilic molecule. We have successfully tried a copolymer of polylysine and polyphenylalanine, and obtained improved binding of luciferase. This increase in the adsorption yield is explained by the dual hydrophilic and hydrophobic character of this copolymer, which will hence bind well to the wall of hydrophobic polystyrene through its hydrophobic portion while maintaining the hydrophilic side towards the solution, on which wall the luciferase will become adsorbed. The adsorption yield is hence increased by using a copolymer of hydrophilic polylysine and another, more hydrophobic amino acid. Other polymers of charged hydrophilic amino acids, such as polyhistidine, a copolymer of polyhistidine, polyarginine or a copolymer of polyarginine could also replace the polylysine.

The advantages of this invention are to keep sensitivity and specificity of the luciferase system described above, but to avoid the problems of retention of light and diffusion of substrate caused by the use of the porous support. In the case proposed here, the enzyme is immediately in contact with the reaction solution. Compared with the assay system in a continuous-flow cell developed by Kricka et al. (above), our invention has the advantage of being simpler, of being immediately applicable to the photometers currently on the market and of not having to take into account the requirements imposed by continuous-flow assays: constant flow, suitably modified measuring cell, difficulty of large-scale production.

Compared with the proposal of Mookambeswaren and Sunanda, our invention makes it possible to use immediately the support used for the assay (tube or strip) and to adsorb the enzyme directly on this support via a hydrophilic molecule. We avoid, on the one hand, the covalent modification of the enzyme, which is especially sensitive to chemical coupling agents, and the support used is directly that which is used for the detection apparatus, i.e. a tube for a photometer or a strip for the flat detector, and this enables a ready-to-use assay system to be produced and greatly facilitates the industrial application.

The present invention consists in immobilizing, on the tube or strip which will be introduced into the photometer or placed in front of any other apparatus for measuring photons, a luciferase with, if necessary, one of the NAD(P)H:FMN oxidoreductases and optionally one or more other dehydrogenases or kinases. The tube coated in this manner can be used for assaying the substrate of the dehydrogenases or kinases, the enzymes themselves or an inhibitor of these latter.

For this purpose, it is necessary to add in the requisite proportions, depending on the objective sought, the substrate of a dehydrogenase (or kinase), and NAD (or NADP or ADP), FMN (or nothing) and the substrate of luciferase, usually decanal, these molecules usually being added in a buffer in the presence of molecules which stabilize the enzymes. As a general rule, the test molecule is introduced in a limiting amount with respect to the other constituents of the system. The light emitted will be measured and usually integrated during a given period, in order to increase the accuracy of the assay.

There is a large number of NAD- or NADP-dependent dehydrogenases which can be used consecutively with the NAD(P)H:FMN oxidoreductase and luciferase; by way of example, we mention a few of these below:
 lactose dehydrogenase
 D-Glucose dehydrogenase
 $\beta$-D-Galactose dehydrogenase
 Glucose-6-phosphate dehydrogenase
 Mannitol dehydrogenase
 Mannitol-1-P dehydrogenase
 Sorbitol dehydrogenase
 Polyol dehydrogenase
 Pentitol dehydrogenase
 D-Xylitol dehydrogenase
 2,3-cis-Polyol dehydrogenase
 L-Threonic acid dehydrogenase
 Lipoyl dehydrogenase
 Lactate dehydrogenase
 Glyoxylate dehydrogenase
 Formaldehyde dehydrogenase
 Formate dehydrogenase
 Aldehyde dehydrogenase
 Alcohol dehydrogenase
 Acetaldehyde dehydrogenase
 Fucose dehydrogenase
 3-$\alpha$-Hydroxysteroid dehydrogenase
 $\beta$-Hydroxysteroid dehydrogenase
 7-$\alpha$-Hydroxysteroid dehydrogenase
 3-$\alpha$-20$\beta$-Hydroxysteroid dehydrogenase We give below an example of assay of lactate dehydrogenase and of testosterone using $\beta$-hydroxysteroid dehydrogenase. We have shown that the assay of this enzyme could be used for measuring the concentration of an inhibitor of this enzyme, such as diethylstilboestrol (DES). The relationship between the amount of DES and the percentage inhibition of $\beta$-hydroxysteroid dehydrogenase is not linear, but the assay of the inhibitor can nevertheless be accomplished by reference to a calibration curve produced with a standard DES preparation.

There is also a large number of kinases which can be used consecutively with the ATP-dependent luciferase. By way of example, we shall mention a few of these below:
 Acetate kinase
 Pyruvate kinase
 Phosphoglycerate kinase These kinases can be used co-immobilized with the luciferase, or free in solution or alternatively bound to another protein whose concentration it is desired to measure. For example, the kinase can be measured while it is bound to an antibody. This also applies to the dehydrogenases mentioned above.

This list, while not exhaustive, shows the variety of substrates and enzymes which can be assayed by application of the method. The tubes prepared in the manner described can be lyophilized and stored for long periods while retaining a substantial part of their activity.

EXAMPLE 1

Assay of NADH and NADPH

In this example, we describe in detail the insolubilization of luciferase and of NADH:FMN oxidoreductase. This insolubilization was optimized in respect of various parameters: type of support, use of polylysine, concentration of poly-L-lysine, pH of binding of the enzymes, stabilization of the enzymes. In effect, the adsorption of these two enzymes serves as a basis for extending the discovery in conjunction with other dehydrogenases.

We used polystyrene tubes specially designed for their high adsorption power (Startube, NUNC, Roskilde, Denmark). The adsorption of the poly-L-lysine was carried out by adding per tube 0.5 ml of poly-L-lysine solution at a concentration of 80 $\mu$g/ml in a solution of 10 mmol/l NaCl and 50 mmol/l Na phosphate, pH 8. The tubes are incubated for 1 hour at 20° C. with a rotation of 5 revolutions per minute, and then rinsed 3 times with 50 mmol/l Na phosphate buffer at pH 7.5. The enzyme solution (0.2 ml), containing 0.5 mg/ml of luciferase extracted from *Vibrio harveyi* (Sigma, St. Louis, Mo. L 1637) and 1 unit of NAD(P)H:FMN oxidoreductase extracted from *Photobacterium fischeri* (Sigma, cat. 476–480) dissolved in 50 mmol/l Na phosphate buffer at pH 7.5 and containing 2 mmol/l of dithiothreitol, is then added to the tube and incubated for 30 min at 4° C. under rotation of 5 revolutions per minute. The tubes are rinsed twice in 10 mmol/l Na phosphate buffer at pH 7.5 containing 5 mg/ml of bovine serum albumin and 2 mmol/l of dithiothreitol, and stored in this buffer.

For the assay, the reaction volume of 0.5 ml comprises 2.5 $\mu$mol/l of FMN, 0.0005% of decanal, 2 mmol/l of dithiothreitol, 5 mg/ml of bovine serum albumin, and NADH in increasing concentrations in 10 mmol/l Na phosphate buffer at pH 7.5. The maximal emission of light was measured. It is found that this light emission is proportional to the concentration of NADH present in the reaction medium for a concentration region ranging from 1 to $20,000 \times 10^{-12}$ moles in the test. The number of photons emitted per second at the maximum intensity ranges from 20 to 10,000.

EXAMPLE 2

Assay of a dehydrogenase

In this example, we shall use the tubes on which the luciferase and NADH:FMN oxidoreductase have been adsorbed as described in Example 1, but they will be used for assaying lactate dehydrogenase in solution. For this purpose, the substrates will be added in excess such that the concentration of the enzyme is the limiting factor. The reaction solution of 0.5 ml contains 2.5 $\mu$mol/l of FMN, 0.0005% of decanal, 2 mmol/l of dithiothreitol, 5 mg/ml of bovine serum albumin, 0.3 mmol/l of NAD+ and 0.01 mol/l of L-lactate, and various concentrations of lactate dehydrogenase. The light emitted is measured and integrated during 60 sec. The assay enables lactate dehydrogenase to be measured in a concentration region ranging from $2 \times 10^{-15}$ to $50 \times 10^{-15}$ moles in the test.

EXAMPLE 3

Assay of the substrate of a dehydrogenase

In this example, the three enzymes luciferase, NADH:FMN oxidoreductase and β-hydroxysteroid dehydrogenase will be immobilized on the tube in order to carry out the assay of testosterone.

The adsorption of polylysine and the enzymes on the tube is carried out as described in Example 1, but the enzyme solution contains 0.075 units/ml of β-hydroxysteroid dehydrogenase. For the assay of testosterone, the tubes contain 0.5 ml of 10 mmol/l Na phosphate buffer at pH 7 and 25 μmol/l of FMN, 0.0001% of decanal, 5 mg/ml of bovine serum albumin, 2 mmol/l of dithiothreitol, 1.2 mmol/l of NAD and various concentrations of testosterone. The light intensity is measured and integrated during 60 sec. The testosterone can be measured in a concentration region ranging from $5 \times 10^{-11}$ to $5 \times 10^{-9}$ moles in the reaction solution.

EXAMPLE 4

Assay of ATP by immobilization of ATP-dependent luciferase

The polystyrene tubes having a high adsorption power (Startube, NUNC, Roskilde, Denmark) were incubated overnight at 4° C. with a rotation of 5 revolutions per minute for 30 min in the presence of a solution of poly(lysine-phenylalanine) at a concentration of 80 μg/ml in a solution buffered to pH 8 with 0.05 mol/l phosphate buffer. The tubes are then rinsed twice with this same buffer. The solution (0.2 ml) of luciferase extracted from *Photinus pyralis* (Sigma St Louis, Mo.) contains 40 μg/ml and immunoglobulins G at a concentration of 0.1 mg/ml dissolved in 0.05 mol/l Tris-acetate buffer, 60 μmol/l dithiothreitol, and is incubated for 30 minutes at 4° C. under rotation of 5 revolutions per minute. The tubes are rinsed twice in the enzyme immobilization buffer.

For the assay, the reaction volume of 0.5 ml comprises 400 μl of 25 mmol/l Tris-acetate buffer, pH 7.75, 75 μmol/l dithiothreitol, 125 μmol/l EDTA, 6.25 mmol/l MgCl$_2$ and $7.5 \times 10^{-5}$ mol/l luciferin.

The reaction is started with 100 μl of solution of increasing concentrations of ATP. The light emission is proportional to the concentration of ATP in a concentration region ranging from 1 to $10,000 \times 10^{-13}$ mol/l.

EXAMPLE 5

Assay of kinase

As an example of kinase assay, we used acetate kinase which catalyses the following reaction:

acetylphosphate + ADP → ATP + acetate

This enzyme can be extracted from thermophilic bacteria (*Bacillus stearothermophilus*) and is especially stable. The optimal conditions for bioluminescence assay of this kinase are as follows:

400 μl of 25 mmol/l Tris-acetate buffer, pH 7.75, 0.125 μmol/l EDTA, 75 μmol/l dithiothreitol, 6.25 mmol/l MgCl$_2$, $7.5 \times 10^{-5}$ mol/l luciferin, 1 mmol/l acetylphosphate; the reaction is started with $10^{-6}$ mol/l ADP (100 μl), the assay of the ATP produced being measured by the ATP-dependent luciferase immobilized on the polystyrene tube. Under these conditions, amounts as small as $10^{-17}$ and $10^{-18}$ μmol of kinase can be assayed in this manner.

I claim:

1. An immobilized enzyme device, comprising: a transparent hydrophobic plastic support; a layer of an amino acid polymer coating the support, said amino acid polymer having hydrophobic portions and hydrophilic portions and said amino acid polymer being oriented so that the hydrophobic portions of the polymer are bound to the support and the hydrophilic portions of the polymer extend outwardly from the support; and an enzyme composition adsorbed to the hydrophilic portions of the polymer, said composition comprising a luciferase.

2. The device of claim 1, wherein the transparent hydrophobic plastic substrate comprises polystyrene.

3. The device of claim 1, wherein the amino acid polymer comprises polylysine.

4. The device of claim 1, wherein the amino acid polymer comprises a copolymer of polylysine, polyarginine, or polyhistidine and a hydrophobic amino acid polymer.

5. The device of claim 4, wherein the amino acid polymer comprises a copolymer of polylysine and polyphenylalanine.

6. The device of claim 1, wherein the enzyme composition further comprises NADH:FMN oxidoreductase or NADPH:FMN oxidoreductase.

7. The device of claim 1 wherein the enzyme composition further comprises a dehydrogenase or a kinase.

8. A method for making an immobilized enzyme device comprising: coating a transparent hydrophobic plastic support with a layer of an amino acid polymer to form a pretreated support, said amino acid polymer having hydrophobic portions and having hydrophilic portions and amino acid polymer being oriented so that the hydrophobic portions of the polymer are bound to the hydrophobic plastic support and the hydrophilic portions of the polymer extend outwardly from the plastic support; immobilizing an enzyme composition on the precoated support by adsorbing the enzyme composition to the hydrophilic portions of the amino acid polymer, said enzyme composition comprising a luciferase.

9. The method of claim 8, further comprising the step of lyophilizing the immobilized enzyme composition.

10. An immobilized enzyme device made by the process of claim 8.

11. The method of claim 8, wherein the transparent hydrophobic plastic substrate comprises polystyrene.

12. The method of claim 8, wherein the amino acid polymer comprises polylysine.

13. The method of claim 8, wherein the amino acid polymer comprises a copolymer of polylysine, polyarganine or polyhistidine and a hydrophobic amino acid polymer.

14. The method of claim 13, wherein the amino acid polymer comprises a copolymer of polylysine and polyphenylalanine.

15. The method of claim 8, wherein the enzyme composition further comprises NADH:FMN oxidoreductase or NADPH:FMN oxidoreductase.

16. The method of claim 8, wherein the enzyme composition further comprises a dehydrogenase or a kinase.

17. A method for determining a test enzyme in a test solution, comprising:

contacting an immobilized enzyme device with a test solution,
said immobilized enzyme device comprises:
a transparent hydrophobic plastic support;
a layer of an amino acid polymer coating the support, said amino acid polymer having hydrophobic portions and hydrophilic portions and said amino acid polymer being oriented so that the hydrophobic portions of the polymer are bound to the support and the hydrophilic portions of the polymer extend outwardly from the support; and
an enzyme composition adsorbed to the hydrophilic portions of the polymer, said composition comprising a luciferase; and
said test solution comprising:
the test enzyme and chemical species that enzymatically react with the test enzyme and the luciferase to emit photons;
detecting photoemission from the contacted test solution; and
quantifying the photoemission to determine the test enzyme in the test solution.

18. The method of claim 17, wherein the chemical species comprise a substrate of the test enzyme, a substrate of the luciferase and ADP.

19. The method of claim 17, wherein the test enzyme is a kinase.

20. The method of claim 17, wherein the enzyme composition further comprises NADH:FMN oxidoreductase or NADPH:FMN oxidoreductase.

21. The method of claim 20, wherein the chemical species comprise a substrate of the test enzyme, a substrate of the luciferase, FMN and NAD or NADP.

22. The method of claim 17, wherein the test enzyme is a dehydrogenase.

23. The method of claim 17, wherein the test enzyme is conjugated with a protein and determining the test enzyme allows determination of the protein.

24. The method of claim 17, wherein the test enzyme is conjugated with an antibody and determining the test enzyme allows determination of the antibody.

25. A method for determining a substrate of a test enzyme, comprising:
contacting an immobilized enzyme device with a test solution,
said immobilized enzyme device comprising:
a transparent hydrophobic plastic support;
a layer of an amino acid polymer coating the support, said amino acid polymer having hydrophobic portions and hydrophilic portions and said amino acid polymer being oriented so that the hydrophobic portions of the polymer are bound to the support and the hydrophilic portions of the polymer extend outwardly from the support; and
an enzyme composition adsorbed to the hydrophilic portions of the polymer, said composition comprising a luciferase and the test enzyme; and said test solution comprising:
the substrate of the test enzyme, and chemical species that enzymatically react with the test enzyme, and the luciferase to emit photons;
detecting the photoemission from the contacted test solution; and
quantifying the photoemission to determine the substrate of the test enzyme.

26. The method of claim 25, wherein the chemical species comprise a substrate for the luciferase and ADP.

27. The method of claim 25, wherein the enzyme composition further comprises NADH:FMN oxidoreductase or NADPH:FMN oxidoreductase.

28. The method of claim 25, wherein the chemical species comprise a substrate of the luciferase, FMN and NAD or NADP.

29. A method for determining an inhibitor of a test enzyme, comprising:
contacting an immobilized enzyme device with a test solution,
said immobilized enzyme device comprises:
a transparent hydrophobic plastic support;
a layer of an amino acid polymer coating the support, said amino acid polymer having hydrophobic portions and hydrophilic portions and said amino acid polymer being oriented so that the hydrophobic portions of the polymer are bound to the support and the hydrophilic portions of the polymer extend outwardly from the support; and
an enzyme composition adsorbed to the hydrophilic portions of the polymer, said enzyme composition comprising luciferase and the test enzyme, said test solution comprising: the inhibitor of the test enzyme and chemical species that enzymatically react with the test enzyme and the luciferase to emit photons;
detecting photoemission from the contacted test solution;
quantifying the photoemission; and
determining the inhibitor by comparing photoemission by the contacted test solution to photoemission by a standard solution comprising said chemical species and a known concentration of said inhibitor.

30. The method of claim 29, wherein the chemical species comprise a substrate of the luciferase and ADP.

31. The method of claim 29, wherein the enzyme composition further comprises NADH:FMN oxidoreductase or NADPH:FMN oxidoreductase.

32. The method of claim 31, wherein the chemical species further comprise a substrate of the luciferase, FMN and NAD or NADP.

33. A method for determining NADH or NADPH in a test solution, comprising:
contacting an immobilized enzyme device with a test solution;
said immobilized enzyme device comprising:
a transparent hydrophobic plastic support;
a layer of an amino acid polymer coating the support, said amino acid polymer having hydrophobic portions and hydrophilic portions and said amino acid polymer being oriented so that the hydrophobic portions of the polymer are bound to the support and the hydrophilic portions of the polymer extend outwardly from the support; and
an enzyme composition adsorbed to the hydrophilic portions of the polymer, said composition comprising a luciferase and either NADH:FMN oxidoreductase or NADPH:FMN oxidoreductase; and
said test solution comprising:
NADH or NADPH, FMN and a substrate for the luciferase; and so as to emit photons detecting photoemission from the contacted test solution; and quantifying the photoemission to determine the NADH or NADPH in the test solution.

34. A method for determining ATP in a test solution, comprising:

contacting an immobilized enzyme device with a test solution, said immobilized enzyme device comprising:

a transparent hydrophobic plastic support;

a layer of an amino acid polymer coating the support, said amino acid polymer having hydrophobic portions and hydrophilic portions and said amino acid polymer being oriented so that the hydrophobic portions of the polymer are bound to the support and the hydrophilic portions of the polymer extend outwardly from the support; and an enzyme composition adsorbed to the hydrophilic portions of the polymer, said composition comprising a luciferase; and said test solution comprising ATP and a substrate for the luciferase so as to emit photons, detecting photoemission from the contacted test solution; and quantifying the photoemission to determine the ATP in test solution.

* * * * *